(12) United States Patent
Van Der Scheer et al.

(10) Patent No.: US 11,759,225 B2
(45) Date of Patent: Sep. 19, 2023

(54) APPARATUS FOR CALLUS REMOVAL

(71) Applicant: KONINKLIJKE PHILIPS N.V., Eindhoven (NL)

(72) Inventors: Robbert Freerk Johan Van Der Scheer, Groningen (NL); Joost Tomas Glazenburg, Groningen (NL); Maurits Koenen, Drachten (NL); Harold Wolf, Oranje (NL); Johannes Beugels, Peize (NL); Adarsh Shrivastava, Drachten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 518 days.

(21) Appl. No.: 16/348,888

(22) PCT Filed: Nov. 9, 2017

(86) PCT No.: PCT/EP2017/078687
§ 371 (c)(1),
(2) Date: May 10, 2019

(87) PCT Pub. No.: WO2018/087196
PCT Pub. Date: May 17, 2018

(65) Prior Publication Data
US 2019/0262021 A1 Aug. 29, 2019

(30) Foreign Application Priority Data
Nov. 11, 2016 (EP) ..................... 16198521

(51) Int. Cl.
*A61B 17/32* (2006.01)
*A46B 13/00* (2006.01)
(Continued)

(52) U.S. Cl.
CPC ............ *A61B 17/32* (2013.01); *A46B 13/008* (2013.01); *A46B 13/02* (2013.01); *A61B 17/54* (2013.01);
(Continued)

(58) Field of Classification Search
CPC ..... A46B 13/00; A46B 13/001; A46B 13/003; A46B 13/005; A46B 13/006;
(Continued)

(56) References Cited

U.S. PATENT DOCUMENTS 1,915,305 A * 6/1933 Gallagher .............. A45D 29/14
132/75.8
2,714,788 A 8/1955 Giovanna
(Continued)

FOREIGN PATENT DOCUMENTS

EP 2245955 A1 11/2010
GB 340377 A 1/1931
(Continued)

*Primary Examiner* — Martin T Ton (57) ABSTRACT

The invention relates to a skin treatment device for removing callus from the skin by an abrasive treatment, comprising a housing with a handle section (110), a skin treatment element (120) rotatable around a rotational axis (101) and a protective rim (130). Said protective rim circumferentially encases said skin treatment element partially over an angular range of more than 120° and less than 330° about said rotational axis such that a circumferential abrasive treatment surface protrudes from the protective rim in an area extending over an angular range of 30° to 240°.

20 Claims, 9 Drawing Sheets

(51) Int. Cl.
*A46B 13/02* (2006.01)
*A61B 17/54* (2006.01)
A61B 90/00 (2016.01)
A61B 17/00 (2006.01)
A61B 17/34 (2006.01)

(52) U.S. Cl.
CPC ... *A46B 2200/1006* (2013.01); *A61B 17/3494* (2013.01); *A61B 2017/00398* (2013.01); *A61B 2017/00473* (2013.01); *A61B 2017/00734* (2013.01); *A61B 2017/00761* (2013.01); *A61B 2017/320004* (2013.01); *A61B 2017/320012* (2013.01); *A61B 2090/08021* (2016.02); *A61B 2217/005* (2013.01)

(58) Field of Classification Search
CPC .................. A46B 13/008; A46B 13/02; A46B 2200/1006; A61B 17/54; A61B 2017/00761; A61B 2017/320004; A61B 2017/320008; A61B 2017/320012; A45D 2200/1054
See application file for complete search history.

(56) References Cited

U.S. PATENT DOCUMENTS

| | | | |
|---|---|---|---|
| 2,867,214 A | 1/1959 | Wilson | |
| 2,881,763 A | 4/1959 | Robbins | |
| 2,921,585 A | 1/1960 | Schumann | |
| 3,937,222 A | 2/1976 | Banko | |
| 4,972,589 A * | 11/1990 | Povleski | B23B 45/003 30/122 |
| 6,139,553 A | 10/2000 | Dotan | |
| 6,423,078 B1 * | 7/2002 | Bays | A61B 17/32 606/131 |
| 6,732,394 B1 | 5/2004 | Waterman | |
| 8,137,363 B2 * | 3/2012 | Cho | A61B 17/54 606/131 |
| D784,620 S * | 4/2017 | Kadaja | D28/59 |
| D848,677 S * | 5/2019 | Thalmann | D28/58 |
| 2003/0136011 A1 * | 7/2003 | Refson | B27B 5/32 30/391 |
| 2005/0234477 A1 * | 10/2005 | Brown | A61B 17/54 606/131 |
| 2006/0253125 A1 | 11/2006 | Ignon | |
| 2007/0221238 A1 | 9/2007 | Tran | |
| 2008/0255586 A1 * | 10/2008 | Greenberg | A61B 17/54 606/131 |
| 2009/0198198 A1 | 8/2009 | Gardner | |
| 2010/0168626 A1 | 7/2010 | Gubernick | |
| 2010/0198119 A1 | 8/2010 | Gubernick | |
| 2011/0270274 A1 | 11/2011 | Hull | |
| 2013/0345721 A1 | 12/2013 | Menke | |
| 2014/0249548 A1 | 9/2014 | Hull | |
| 2014/0305458 A1 | 10/2014 | Brewer | |
| 2015/0150353 A1 * | 6/2015 | Yiu | A45D 29/14 132/75.6 |
| 2017/0340356 A1 * | 11/2017 | Presser | A61B 17/545 |

FOREIGN PATENT DOCUMENTS

| | | |
|---|---|---|
| WO | 2005109996 A2 | 11/2005 |
| WO | 2006002489 A1 | 1/2006 |
| WO | 2008052866 A1 | 5/2008 |
| WO | 2009148729 A2 | 12/2009 |
| WO | 2015082995 A1 | 6/2015 |

* cited by examiner

APPARATUS FOR CALLUS REMOVAL

This application is the U.S. National Phase application under 35 U.S.C. § 371 of International Application No. PCT/EP2017/078687, filed on Nov. 9, 2017 and International Application No. 16198521.3, filed Nov. 11, 2016. These applications are hereby incorporated by reference herein.

FIELD OF THE INVENTION

The invention relates to a skin treatment device for removing callus from the skin by an abrasive treatment.

BACKGROUND OF THE INVENTION

Callus removal from the skin can generally be done manually using appropriate hand tools like files, pumice stones and creams. A more effective and time-saving way to remove callus from the skin is the use of electrically driven devices having an abrasive surface which is driven into motion relative to the skin. The callus can be ground off by such devices. Predominantly, such devices are configured such that a roller with an abrasive circumferential surface is driven to rotate about an axis and is mounted to a handle extending in a direction perpendicular to the axis. The roller can be guided across the skin with the rotating axis of the roller being parallel to the skin surface. In this way, the circumferential surface of the roller abrades and grinds off the callus.

According to another setup of such a callus removal device, the abrasive surface is provided on an axial surface of a disk which is driven into rotation by a motor. The axial surface of the disk may be planar and can be brought into contact with the skin to produce the grinding and abrading effect. In this configuration, the rotational axis is perpendicular to the skin surface during use of the device.

Various problems are related to such callus removal devices. The configuration having a roller with a circumferential abrasive surface was found to produce significant local abrasion but is difficult to handle and control in such a way that a constant abrasion over a larger area of the skin is achieved. Devices having a disk-shaped abrasive element are difficult to control, since in conditions where the disk is in contact with the skin at a slightly angular orientation, i.e. with the rotational axis not being exactly perpendicular to the skin surface, a torsional force will be produced by such partial contact of the rotating abrasive surface, which forces the device to move across the skin out of the region where it was initially positioned. In such conditions, it will be difficult for the user to control the device and exactly maintain its position.

U.S. 2014/0305458 A1 and WO 2006/002489 A1 disclose such tools for performing an abrasive treatment of the skin using a rotating disk with an axial abrasive surface. These devices comprise a housing having a rim encasing the disk such that the whole circumference of the disk is covered by said rim. In this way, the effect of angular, i.e. non-planar, positioning of the disk surface on the skin is reduced such that the occurrence of undesired torsional forces effecting a movement of the disk across the skin is significantly reduced. However, such a setup shown in these devices was found to decrease the efficiency of callus removal. The efficiency is understood to be defined by the volume or mass of callus removed within a time period. Furthermore, precision treatment of a small skin region is not possible with such a configuration.

WO 2015/082995 A1 discloses a cosmetic device including a housing and a drum assembly having an abrasive outer circumferential surface rotatably coupled to the housing. In an embodiment a shield or guard may be coupled to the housing and extend about a portion of the drum assembly. Various embodiments of the drum assembly are disclosed, including a drum assembly comprising an additional flat or disc-shaped abrasive portion on one end of the drum assembly.

It is an object of the invention to provide a callus removal device which overcomes the above explained problems and which allows precision treatment of the skin.

SUMMARY OF THE INVENTION

This problem is solved according to the invention by a skin treatment device comprising a housing with a handle section, a skin treatment element rotatable around a rotational axis, a protective rim arranged stationary at said housing and having an axial skin contact surface configured and arranged to support the skin of a user during use, wherein said skin treatment element is rotatable in relation to said protective rim, and a drive mechanism for driving the skin treatment element in a rotational movement about said rotational axis, wherein said skin treatment element has an axial abrasive treatment surface which is accessible for skin treatment through an axial opening of the protective rim, wherein said axial opening extends over an angular range of 360° about said rotational axis, wherein said skin treatment element further has a circumferential abrasive treatment surface having an at least partially radial orientation, wherein said protective rim circumferentially encases said skin treatment element partially over an angular range of more than 120° and less than 330° about said rotational axis, such that the circumferential abrasive treatment surface is accessible for skin treatment in an area extending over an angular range of 30° to 240° about the rotational axis.

The skin treatment device according to the invention comprises a skin treatment element which has an axial abrasive treatment surface and a circumferential abrasive treatment surface. An axial abrasive treatment surface is understood to be a treatment surface oriented approximately perpendicularly to an axial direction, like the front side of a rotational disk, or at least having a surface section with such an orientation. A circumferential abrasive treatment surface is understood to be oriented such that a vector orthogonal to that surface has a component which is parallel to a radial direction, like the peripheral edge surface of a rotational disk. The axial direction is understood to be parallel to the rotational axis, whilst the radial direction is understood to be orthogonal to the rotational axis. The axial abrasive treatment surface may have a flat or curved shape, like a concave or convex shape. The circumferential abrasive treatment surface may have a cylindrical or conical shape or it may have a curved sectional shape, in a longitudinal cross section along the rotational axis, with a concave or convex curvature.

It is to be understood that preferably the circumferential abrasive treatment surface and the axial abrasive treatment surface are adjacent to each other such as to form a circular rim which may be sharp-edged, beveled or rounded.

The skin treatment element is driven into a rotational movement about said rotational axis by a drive mechanism. Such rotational movement is understood to be a constant rotation in one direction around the rotational axis, wherein the direction of rotation may be selectable by the user of the device. The rotational movement may alternatively be an oscillatory rotational movement wherein the direction of rotation is frequently changed. The skin treatment device may be configured in such a way that the user can select either a constant rotational movement or an oscillatory rotational movement via a user interface of a control unit incorporated in the device.

The skin treatment device further comprises a drive mechanism. It is understood that such a drive mechanism may comprise a motor incorporated into the housing, but alternatively the motor may be arranged at a distance to the housing and coupled to the skin treatment element via a mechanical coupling element like a flexible shaft. Preferably, the drive mechanism comprises an electric motor. It is further understood that a source of electric energy, like a replaceable or rechargeable battery, may be included in the housing of the device to provide energy to said electric motor.

A protective rim is arranged at the housing of the skin treatment device. The protective rim may be integral with the housing or may be a separate element which is mounted to the housing. The protective rim may be releasably fixed to the housing to allow exchange or replacement of the protective rim. The protective rim does not fully encircle the skin treatment element along its circumferential abrasive treatment surface, but only encircles the skin treatment element partially through an angle of 120° to 330° about the rotational axis. As a result, the skin treatment element is not radially covered by the protective rim over an angular range of at least 30° to 240° about the rotational axis. The wordings "to partially encase over a particular angular range" and "to partially encircle over a particular angular range" used with respect to the protective rim are to be understood to cover both a continuous encasing and encircling throughout the angular extension of said particular angular range, as well as a discontinuous encasing and encircling, wherein the protective rim may comprise openings within said particular angular range or wherein the protective rim has a number of individual rim segments arranged within said particular angular range and separated by openings.

The protective rim has an axial skin contact surface configured and arranged to support the skin of a user during use of the skin treatment device. Similar to the axial abrasive treatment surface of the skin treatment element, an axial skin contact surface is understood to be a skin contact surface oriented approximately perpendicularly to an axial direction, or at least having a surface section with such an orientation, wherein the axial direction is understood to be parallel to the rotational axis.

This specific design of the protective rim was found to prevent significant torsional forces induced by the rotating skin treatment element, even if the axial abrasive treatment surface is positioned in an angular orientation against the skin surface. This is achieved by both preventing contact of the skin treatment element with the skin in such an angular orientation and preventing the corner region of the skin treatment element from contacting the skin. Further, the protective rim facilitates planar positioning of the axial abrasive treatment surface in that it serves as a support on the skin. The skin treatment device according to the invention provides a skin treatment element which may radially protrude from the protective rim such that both the circumferential abrasive treatment surface and the axial abrasive treatment surface can be used for precision treatment of small areas of the skin in this protruding section. In this manner, the skin treatment device offers improved handling, control and efficiency for treating large skin regions but at the same time offers improved precision treatment of small skin regions or of any skin regions which are difficult to reach.

Whilst the circumferential abrasive treatment surface thus can only be reached through a circumferential opening of limited angular extension in the protective rim, the axial abrasive treatment surface can be reached through an opening of the protective rim which extends over the full angular range of 360° about the rotational axis. In particular, the protective rim may have an axial opening through which the axial abrasive treatment surface is accessible, wherein said axial opening is as large as the axial treatment surface.

It is to be understood that the lower limit of the angle through which the rim encircles the skin treatment element about the rotational axis may be selected from 135°, 160°, 180°, or 225°, whilst the upper limit may be selected from 180°, 225°, 275° and 300°, with a corresponding range of the section of the skin treatment element not being radially covered.

Generally, the protective rim has a rather smooth skin contact surface as compared to the abrasive treatment surfaces of the skin treatment element so as to facilitate gliding of the skin treatment device across the skin surface in the course of a skin treatment.

According to a first preferred embodiment, an axial adjustment of a position of said skin treatment element and a position of said protective rim relative to each other in an axial direction parallel to said rotational axis is provided such that the position of the axial abrasive treatment surface in relation to the protective rim can be altered in said axial direction. This embodiment allows for axial adjustment of the position of the protective rim with respect to the position of the skin treatment element. Generally, this can be achieved by either mounting the protective rim in such a way that it can be moved in the axial direction parallel to the rotational axis in relation to the housing while the skin treatment element is mounted in a fixed axial position at the housing or, vice versa, in such a way that the skin treatment element is able to perform an axial movement with respect to the housing while the protective rim is mounted in a fixed axial position at the housing. Alternatively, both the protective rim and the skin treatment element are able to perform an axial movement relative to the housing. In many applications it is preferred that the axial abrasive treatment surface of the skin treatment element is flush with the axial skin contact surface of the protective rim such that, when positioning the axial abrasive treatment surface of the skin treatment element onto a flat surface, the protective rim is in contact with said flat surface. However, in some applications a protruding position of the axial abrasive treatment surface of the skin treatment element in relation to the protective rim is preferred whilst in other specific applications a recessed position of the axial abrasive treatment surface in relation to the protective rim is preferred. For example, a protruding position of the axial abrasive treatment surface will produce a higher rate of abrasion and thus may provide improved efficiency of the ablation rate of callus material while at the same time increasing the tendency of torsional forces occurring when the axial abrasive treatment surface is in an angular position to the skin. Vice versa, a recessed position of the axial abrasive treatment surface will facilitate the handling and better prevent occurrence of any torsional forces but will at the same time reduce the ablation rate. This preferred embodiment can be further improved in that said axial adjustment is provided by the protective rim being selected from a number of different, interchangeable protective rims to be mounted to said housing, wherein said interchangeable protective rims have mutually different heights parallel to said rotational axis, and/or the skin treatment element being selected from a number of different, interchangeable skin treatment elements to be mounted to said housing, wherein said interchangeable skin treatment elements have mutually different heights parallel to said rotational axis. According to this embodiment, the skin treatment device according to the invention comprises at least two different protective rims or at least two different skin treatment elements, wherein one of them is mounted to the housing and may be exchanged against the other. For example, a regular protective rim for a flush arrangement of the axial abrasive treatment surface and the protective rim may be included and further a lower protective rim for a protruding arrangement of the axial abrasive treatment surface and a higher protective rim for a recessed arrangement of the axial abrasive treatment surface may be included. According to this embodiment, the protective rims are mounted to the housing via a releasable coupling like e.g. a screwed coupling, a snap connection or any type of form-locking coupling through an elastically movable form-locking member at the protective rim engaging a form-locking counterpart at the housing. Further, or alternatively, a first skin treatment element having a coarse grid size and a second skin treatment element having a fine grid size may be provided, wherein the first skin treatment element has a lower height than the second skin treatment element such that the first skin treatment element is somewhat more recessed in the protective rim than the second skin treatment element with the fine grid size.

It is understood that, besides these protective rims of different heights, further different designs of protective rims which may be mounted to the skin treatment device may be comprised. As an example, a protective rim may be provided having two angular gaps, wherein in said gaps no protective rim encases the skin treatment element. These two angular gaps may preferably be arranged opposite to each other or may be positioned such as to provide a rotational symmetry around the rotational axis.

Further, the preferred embodiment may additionally or alternatively be further improved in that said axial adjustment is provided by said skin treatment element or said protective rim being movable parallel to said rotational axis. As explained hereinbefore, either one of said movements or both could be provided to allow said axial adjustment of the skin treatment element and the protective rim with respect to each other. The movement along the rotational axis may e.g. be provided as a linear translation along the rotational axis or as a screw-type translation along a winding. Further, locking means may be provided to lock a position of the skin treatment element versus the protective rim in a particular axial position with respect to each other.

According to a further preferred embodiment, said protective rim comprises a circumferential inner edge, wherein said circumferential inner edge partially surrounds said skin treatment element and protrudes above or is flush with said axial abrasive treatment surface such that particles thrown radially outward along said axial abrasive skin treatment surface are collected by said inner edge and directed into a particle collecting space. Generally, the inventors observed a malodorous scent occurring frequently when callus is removed by a grinding action. The inventors found that such malodorous scent can be significantly reduced if the particles produced by the grinding removal of the callus are collected in a collecting space rather than allowing these ground-off particles to be thrown away from the device. According to this embodiment, the protective rim provides an additional function in that the protective rim further acts as a catch ring which catches the ground-off particles. This catching function is enabled by the particles being spun off the skin treatment element by centrifugal force in a radial/tangential direction and then hitting the circumferential inner edge such that the particles are collected at said inner edge or the inner edge directs the particles to the particle collecting space. It is understood that the circumferential inner edge may only protrude above the axial abrasive treatment surface over a small distance being in a range of a few millimeters only or even below 1 millimeter. Generally, the small particles thrown radially off the axial abrasive treatment surface will usually be collected together even if such a small protruding distance of the inner edge is provided. The inner edge may be formed such that the particles are directed by the inner edge directly into the collecting space, but the transport of the particles into the collecting space may be supported by other means like e.g. an airflow produced by the axial abrasive treatment surface or a separate fan or blower component. It was found by the inventors that by collecting the particles the malodorous scent can be reduced significantly since these particles were identified to produce the malodorous scent. Further, the embodiment comprising the circumferential inner edge improves the hygienic properties of the device in that no particles, dust and the like are thrown out of the device or the release of such particles and dust is at least significantly reduced.

The embodiment can be further improved by a conveying device for conveying particles collected in said collecting space to a collecting box. Generally, the particles caught by the inner edge may be collected in the collecting space only, which usually is placed close to or adjacent to the inner edge. However, this may require frequent cleaning of the collecting space to remove the particles accumulated therein. According to this preferred embodiment the particles are conveyed out of the collecting space into a collecting box which may have sufficient capacity to avoid the need for frequent cleaning.

While such a conveying device may be a separate unit with a separate drive mechanism, it is in particular preferred that said conveying device is embodied as a fan driven by said drive mechanism. According to this improvement the conveying device is driven by the drive mechanism driving the skin treatment element and thus the need for a second, independent driving means is avoided. The fan preferably provides a radial-axial conveying action to collect the particles from the collecting space and convey these particles to a collecting box in an axial direction. Alternatively, guiding elements at the fan or stationary guiding elements may be provided to create any specific conveying path for the particles from the collecting space to the collecting box. It is understood that the conveying device embodied as a fan may in particular support the collecting of particles in the collecting space by said inner edge in that a suction effect is produced in the gap between the inner edge and the skin treatment element by said fan.

Still further it is preferred that said conveying device is mounted rotatably about said rotational axis and driven synchronously to said skin treatment element. According to this embodiment, the conveying device is mounted coaxially with said skin treatment element and thus may preferably be mounted behind the skin treatment element seen from the axial abrasive treatment surface, thus allowing a simple and robust design of the skin treatment device in the part of the treatment element.

According to a further preferred embodiment, said skin treatment element protrudes radially outward of the housing in said area in which the circumferential abrasive treatment surface is accessible for skin treatment. By virtue of this radial protrusion of the skin treatment element the skin treatment device is particularly adapted for a precision treatment of the skin to allow treatment of skin regions which are small, which are difficult to access or which require particular attention when being treated. The protrusion of the skin treatment element may allow the treatment of the skin with the axial abrasive treatment surface in this protruding section and/or with the circumferential abrasive treatment surface.

According to a further preferred embodiment, said skin treatment element is a disk-shaped abrasive tool having an abrasive treatment surface on an abutting axial surface forming the axial abrasive treatment surface and having an abrasive peripheral edge surface forming the circumferential abrasive treatment surface. This embodiment allows for exchange of the skin treatment element such as to allow additional functionality of the skin treatment device. For this purpose, the skin treatment element may be mounted to a shaft coupled to the drive mechanism in a releasable interlocking action such that two or more different skin treatment elements can alternatively be mounted or to allow replacement of skin treatment elements which have lost their abrading function, are worn or cannot be used for other reasons. It is understood that, with said disk-shaped abrasive tool, the axial abrasive treatment surface and the circumferential abrasive treatment surface may be adjacent to each other forming a circular corner region which may be sharp-edged, beveled or rounded. Further, it is understood that the circumferential abrasive treatment surface may be in an angular arrangement to the axial abrasive treatment surface of 90° or more than 90°, such that the circumferential abrasive treatment surface is oriented in a radial-axial direction. The skin treatment element may for example be exchanged by a brush-type tool, wherein it is understood that the brush-type tool may comprise brushes on an axial treatment surface only or may additionally or only comprise brushes on a circumferential treatment surface such as to allow treatment of large areas and precision treatment of small areas of the skin.

According to a further preferred embodiment:

said handle section extends along a handle axis and said rotational axis is oriented at an angle of more than 20° and less than 90° relative to said handle axis, with the lower limit preferably selected from 31°, 41°, and 51°, and with the upper limit preferably selected from 49°, 59°, and 79°; and said skin treatment element is disk-shaped having an edge between the axial abrasive treatment surface and the circumferential abrasive treatment surface with an edge radius which is more than 0.3 mm and less than 10 mm, with the lower limit preferably selected from 1.1 mm, 2.1 mm, and 2.5 mm, and with the upper limit preferably selected from 2.1 mm, 5.1 mm, and 7.5 mm; and said skin treatment element is disk-shaped having a disk diameter which is more than 25 mm and less than 55 mm, with the lower limit preferably selected from 31 mm and 36 mm, and with the upper limit preferably selected from 29 mm, 39 mm, and 44 mm; and said drive mechanism is adapted to control a rotation speed of said skin treatment element to be more than 200 rpm and less than 1000 rpm, with the lower limit preferably selected from 410 rpm and 610 rpm, and with the upper limit preferably selected from 690 rpm and 890 rpm; and said axial and circumferential abrasive treatment surfaces are configured to form an abrasive surface having a grit size of finer than 80 and coarser than 200 according to the ANSI definition, with the lower limit preferably selected from 105, 115 and 125, and with the upper limit preferably selected from 135, 155 and 185.

According to this preferred embodiment, the handle section is oriented in a specific angular range to the rotational axis. This angular design of the skin treatment element versus the handle was found to facilitate and improve the handling of the skin treatment device such that the user may better control the treatment and conduct a precision treatment with the skin treatment device. It is to be understood that a fixed angle may be provided but, alternatively, the device may be adapted to allow adjustment of said angle within said range by the user, to configure the device for treatment of different skin areas. Further, according to this preferred embodiment, the edge radius of the disk-shaped skin treatment element, the disk diameter of the skin treatment element, the rotational speed of the skin treatment element and the grit size of the abrasive surfaces of the skin treatment element are each selected out of a particular range of parameter values which were identified by the inventors to significantly improve the handling and functionality of the skin treatment device. In particular, these parameters were found to provide an optimum compromise of the ability to perform effective abrasion of callus, conduct a precision treatment and prevent torsional forces occurring in case of angular positioning of the axial abrasive treatment surface onto the skin. In detail, the inventors found that too small an angle between the handle axis and the rotational axis, too high a rotational speed of the disk, too large a disk diameter and too small a grit size, i.e. too coarse the abrasive treatment surfaces, will impair the control and handling of the device in that the device cannot be positioned precisely in a particular skin region and tends to produce torsional forces which cannot be counteracted and controlled well by the user. On the other hand, too large an angle between the handle axis and the rotational axis, too low a disk speed, too small a disk diameter and too large a grit size will impair the efficiency to remove callus. Further, it will be difficult to use the axial abrasive treatment surface of the disk if a large angle of the handle axis to the rotational axis is selected. A rather small disk diameter will not allow the treatment of large skin surfaces for efficient callus removal. Regarding the grit size definition it is understood that according to the ANSI definition applied here, the grit size shall be finer or equal to 100 and shall be coarser or equal to 140. Generally, this ANSI definition is commonly used for characterization of sand paper or any other abrasive surfaces having undefined cutting edges.

It is to be understood that according to a preferred embodiment a specific relation between the grit size and the range of the rotational speed may be provided as an additional functionality. For example, the particular grit size of a skin treatment element may be detected or recognized by a recognition unit incorporated in the device, e.g. by a code or the like provided at the skin treatment element. In case of such recognition the rotation speed may be adjusted to a predetermined value depending on the grit size or may be limited to a predetermined range which best fits the grit size. In general, a smaller grit size may require a smaller rotational speed than a higher grit size.

According to a further preferred embodiment, the skin treatment device may comprise a protective rim element adapted to circumferentially encase said skin treatment element over an angular range of more than 30° and less than 240° about the rotational axis, respectively, to cooperate with said protective rim such as to fully encase said skin treatment element, wherein said protective rim element can be switched from a first position, wherein said skin treatment element is partially encased along its circumference by said protective rim, to a second position, wherein said skin treatment element is fully encased along its circumference by said protective rim and said protective rim element. According to this embodiment, the angular gap of 30° to 240° of the protective rim about the rotational axis may be closed by a separate protective rim element which can be mounted to the housing or the protective rim. As a result, the skin treatment element may be fully surrounded by a protective rim composed of the protective rim and the protective rim element. While such configuration may not allow a precision treatment, it will be useful for treating large skin regions and will help to further reduce the tendency of translational movements across the skin due to torsional forces when positioning the device on the skin in an angular displacement.

It is understood that the protective rim element can be switched from a first to a second position, wherein in said first position the skin treatment element is not entirely encased by the protective rim element but rather only such as to allow a precision treatment using the section of the skin treatment element which is not encased by the protective rim. In the second position, the protective rim element closes the angular gap such that the skin treatment element is fully encircled by the protective rim and the protective rim element along its periphery. In this second position the protective rim element is preferably flush with the protective rim such as to provide a flush contact surface with the skin.

Generally, it is preferred that said switching from said first to said second position and vice versa is provided by said protective rim element being releasably mounted to said housing or being movable relative to said housing. According to this embodiment, the protective rim element may be slid or otherwise moved from the first to the second position and vice versa and will stay mounted to the skin treatment device in both the first and the second position. Alternatively, the skin treatment element may be releasably mounted to the skin treatment device to be in the second position and may be demounted from the skin treatment device to be in the first position.

According to a still further preferred embodiment, said protective rim is movable in a direction parallel to said rotational axis and biased towards an outward position wherein said protective rim axially projects above said skin treatment element along said rotational axis. According to this embodiment, the protective rim is not mounted rigidly to the housing and in relation to the skin treatment element but rather is mounted in such a way that a limited axial movement along the rotational axis can be performed by said protective rim. It is understood that, in case of a protective element being provided, this protective element may perform the same axial movement in a limited range synchronously to the protective rim.

The ability to move along the rotational axis over a limited range enables the handling of the device to be further improved in that the user may control the ablation rate of the device by increasing or decreasing the contact force of the skin treatment device onto the skin. The protective rim is biased towards an outward position which is understood to be a position wherein the protective rim may protrude above or may be flush with the axial abrasive treatment surface. If the user applies the skin treatment device to the skin, the protective rim is pressed inwards against this biasing force such that the skin treatment element will come into close contact with the skin to perform the abrasive function. This abrasive function will be increased by increasing the contact force and thus pushing the protective rim more inwards. At the same time, the protective rim may partially lose its function of exerting increased control if the contact force is increased in that the axial abrasive treatment surface will more and more protrude with respect to the protective rim. By virtue of this, the user may well balance out the compromise of controllability and efficiency of abrasion of the device by controlling the contact force between the device and the skin.

It is understood that the biasing force of the protective rim may be provided by a spring element or by any other elastically deformable element. Further, the protective rim itself may be made from an elastically deformable material.

According to a still further preferred embodiment, said protective rim comprises a plurality of rim segments which are movable relative to each other. Such a plurality of rim segments which are movable relative to each other will allow to adapt the angular or radial extension of the protective rim by moving one or a plurality of said rim segments in relation to one or more other rim segments or a single remaining rim segment. Such movement of a rim segment may be in an axial, radial or axial-radial direction. In particular, the segments may be moved with respect to each other in such a way that a single or a plurality of rim segments are either removed or attached to form part of the protective rim. According to this modification of the embodiment, the rim segments are releasably attached to the housing of the skin treatment device to allow such selective removal and attachment. The embodiment particularly allows to adapt the protective rim to extend over a smaller or larger angular range, but will further allow to modify the protective rim in such a way that it comprises two, three or more protective rim regions which are separated from each other by a gap, wherein said gap may have an angular extension depending on the dimension or number of rim segments which were moved or removed between the rim regions. In particular, the rim segments may be attached to the housing by a releasable form locking interaction.

DETAILED DESCRIPTION OF THE EMBODIMENTS

Figure 1A:
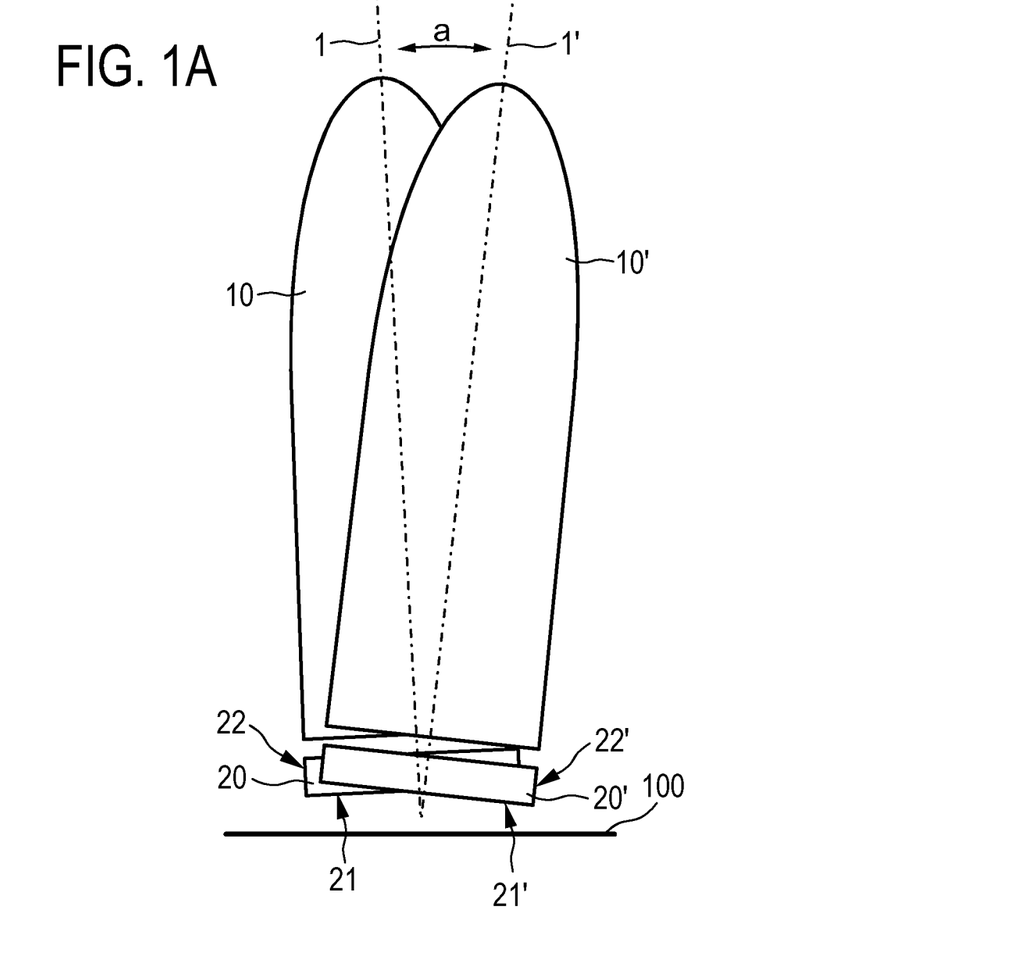
FIG. 1a schematically shows a side view of a skin treatment device in a rectangular and a tilted orientation, FIG. 1b schematically shows the reaction forces in a top view of the disk-shaped skin treatment element of FIG. 1a, FIG. 2 shows a side view of a first embodiment of the skin treatment device according to the invention.

A typical problem associated with callus removal devices employing a disk-shaped rotating skin treatment element is shown in FIGS. 1a,b. As shown, the skin treatment device comprises generally a handle 10 and a disk-shaped treatment element 20 which is mounted at said handle to rotate about a rotational axis 1. As shown in FIG. 1a, the rotational axis 1 may be tilted somewhat to the left in relation to a perpendicular axis on a skin surface 100 to be treated or may be tilted somewhat to the right as depicted by handle 10', disk 20' and rotational axis 1'. Thus, as a result of only a minor angular tilting through an angle α, an axial abrasive treatment surface 21, 21' will no longer be oriented parallel to the skin surface 100. This angular displacement between the axial abrasive treatment surface 21, 21' will produce a torsional force TF or TF', respectively, as shown in the schematic top view of FIG. 1b. Such a torsional force, however, will cause a loss of control with regard to the precise positioning of the device and may produce translational movement across the surface of the skin which is neither desired nor controllable by the user.

Figure 1B:
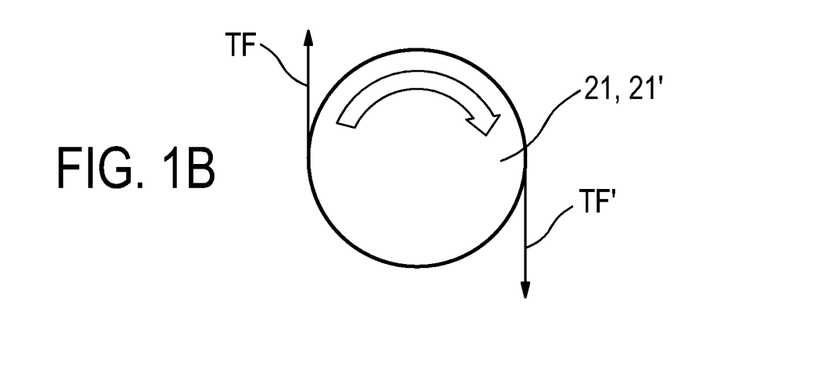

Generally, the reason for such loss of control was found to lie in frictional engagement between only a part of the axial abrasive treatment surface and the skin on the one hand and a local contact over a limited angular range of a circumferential abrasive treatment surface 22, 22' or a corner region between the axial and the circumferential abrasive treatment surfaces on the other hand.

Figure 2:
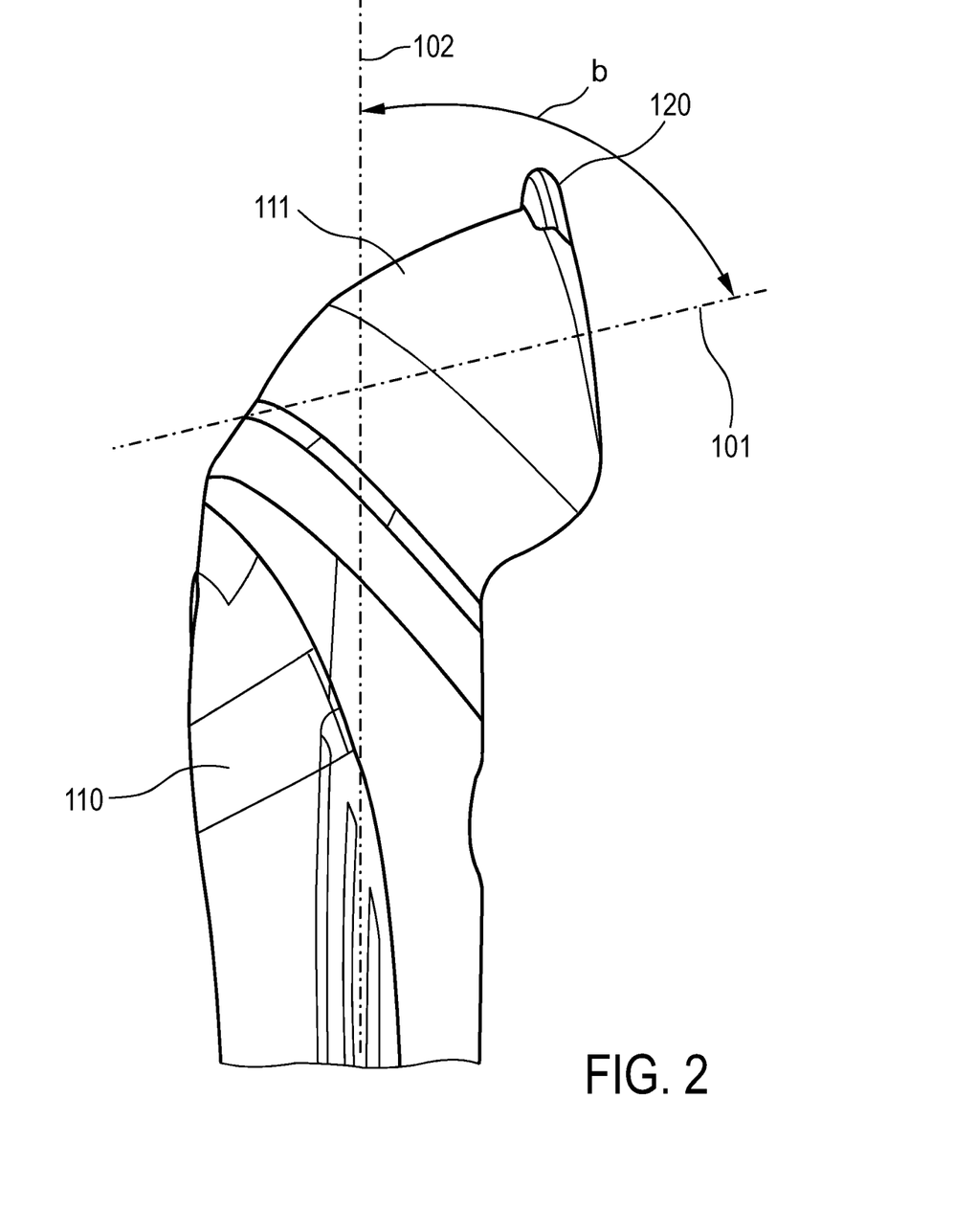

FIG. 2 shows a first embodiment of a skin treatment device according to the invention. The skin treatment device generally comprises a housing incorporating a handle section 110 and a treatment head section 111. The handle section 110 may incorporate an electrical motor, a rechargeable battery coupled to said motor for energy supply, a socket for recharging said battery and a user interface adapted to control the motor. The user interface may comprise an on-off switch and may further comprise control means for adjusting parameters of the electrical motor like rotational speed, direction of rotation, unidirectional or oscillatory motion and the like. Further, a display may be incorporated displaying parameters like rotational speed, type of motion or battery level.

As can be seen in FIG. 2, the treatment head 111 comprises a disk-shaped treatment element 120 at one end. The disk-shaped treatment element is generated for rotational movement about a rotational axis 101. As can be seen, the rotational axis 101 is in angular orientation with respect to a handle axis 102 along which the handle section 110 extends. In the embodiment shown in FIG. 2, the angle β between the rotational axis 101 and the handle axis 102 is about 75°. It is understood that the angle β may preferably be in a range of 40°-90° to allow proper control of the device.

Figure 3:
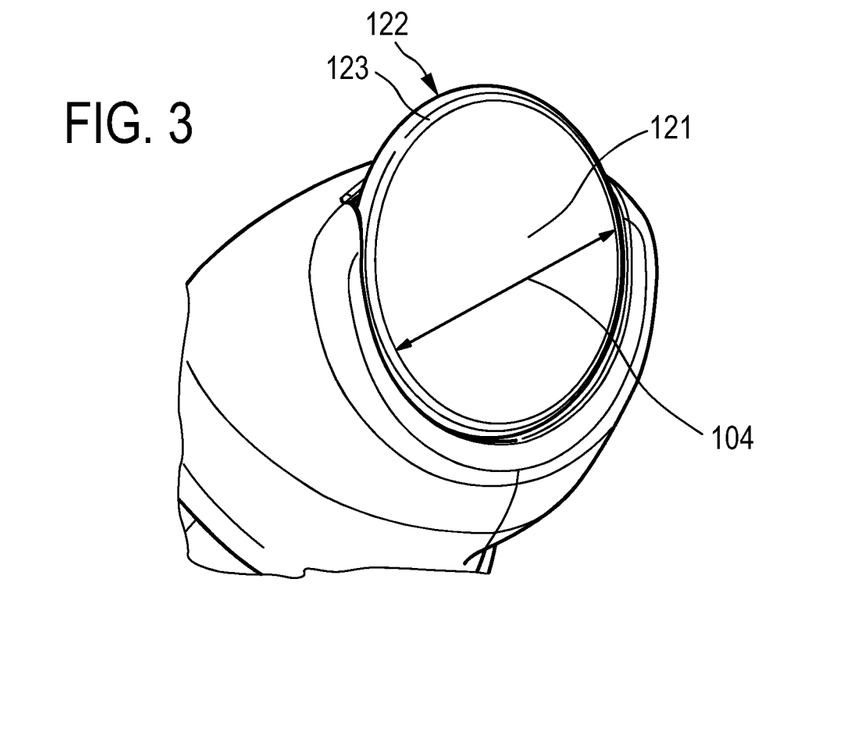
FIG. 3 shows a perspective partial side-top view of the device shown in FIG. 2.
Figure 4:
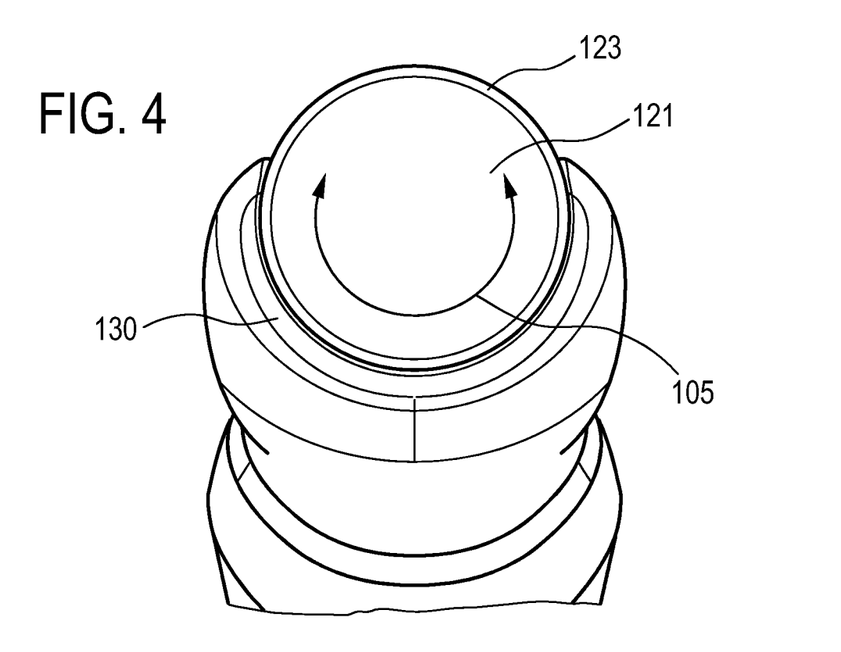
FIG. 4 shows a perspective partial top view of the device of FIG. 2.
Figure 5:
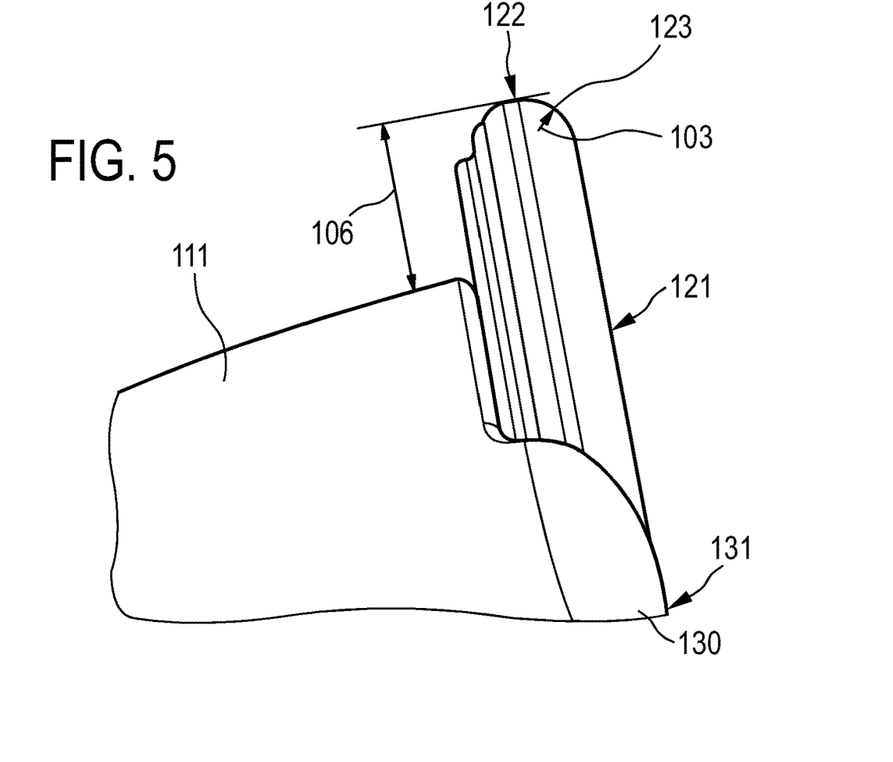
FIG. 5 shows a perspective partial side view of the device of FIG. 2.

As shown in further detail in FIGS. 3-5, the disk-shaped treatment element 120 comprises an axial abrasive treatment surface 121 and a circumferential abrasive treatment surface 122. A circular corner region between these two abrasive treatment surfaces 121, 122 is rounded such as to provide a disk edge radius of 3 mm. It is understood that the disk edge radius may preferably be in a range of 1-5 mm. The disk-shaped treatment element has a disk diameter 104 of 33 mm, wherein the diameter may preferably be selected in a range from 30 to 36 mm. Further, the surface grit size of both the axial abrasive treatment surface 121, the circumferential abrasive treatment surface 122 and the circular corner region 123 is 120 according to the ANSI definition wherein the grit size may preferably be selected in a range of 100-140. The grit size of the circumferential abrasive treatment surface may be different from the grit size of the axial abrasive treatment surface. Further, the grit size of the circular corner region may be different from the grit size of the axial abrasive treatment surface.

A protective rim 130 circumferentially encases the disk-shaped treatment element through a limited angular range 105. The protective rim 130 has an axial smooth skin contact surface 131 which is flush with the axial abrasive treatment surface 121 as can be seen in FIG. 5 in detail. The protective rim 130 extends through an angle β of approximately 225°, wherein the angle β may be selected in a range from 120°-330°.

As a result, the circumferential abrasive treatment surface 122 and the corner region 123 are covered by the protective rim through a large angle and only a small angular region thereof is not covered to enable a skin treatment therein. This small angular region amounts to 135° in the embodiment shown in FIG. 4 but may be in a range of 30° to 240°.

The protective rim is designed as a monolithic part of the housing section of the treatment head. As can be seen in FIG. 5, the disk radially protrudes from the housing section 111 over a distance 106 which may preferably be selected from 4 to 6 mm for sufficient control and precision treatment using the protruding section of the disk-shaped treatment element.

Figure 6:
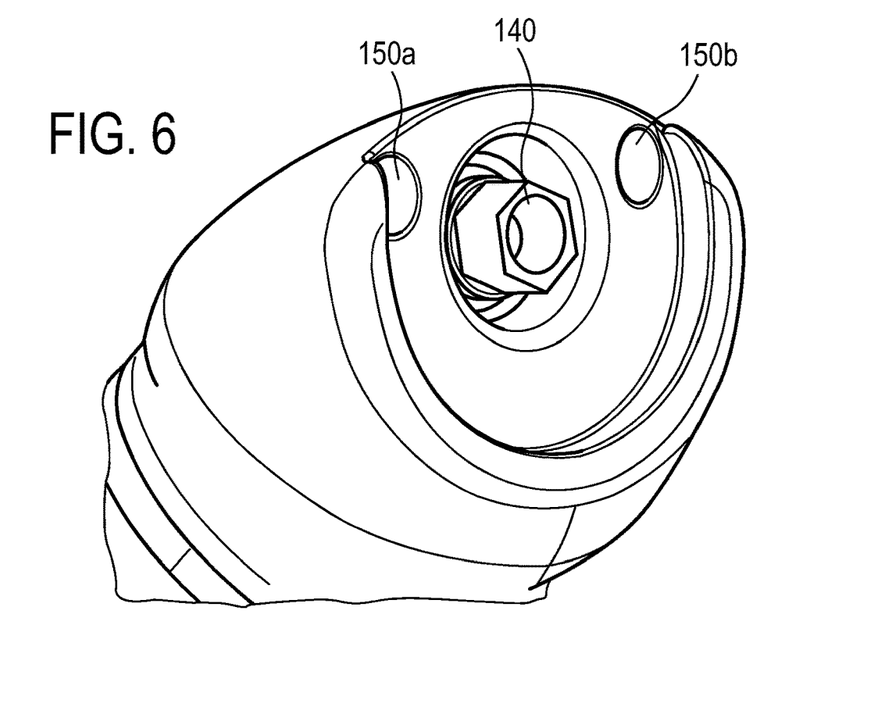
FIG. 6 shows a view according to FIG. 3 with the skin treatment element being removed.

FIG. 6 shows the treatment head according to FIG. 3 with the disk-shaped treatment element 120 being removed. As can be seen, a drive mechanism is incorporated in the device and comprises a form-locking element 140 in the form of a hexagonal cross-sectional member for mounting the disk-shaped treatment element. Further, two suction channels 150a, b can be seen which are designed to remove ground-off particles and dust from the gap between the disk-shaped treatment element and the rim 130. The function of these channels will be explained in detail hereinafter.

Figure 7A:
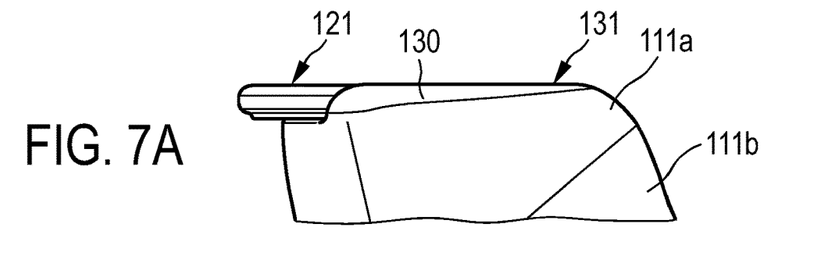
FIGS. 7a-c show perspective views according to FIG. 5 depicting three different adjustments of the skin treatment element with respect to the protective rim.
Figure 7B:
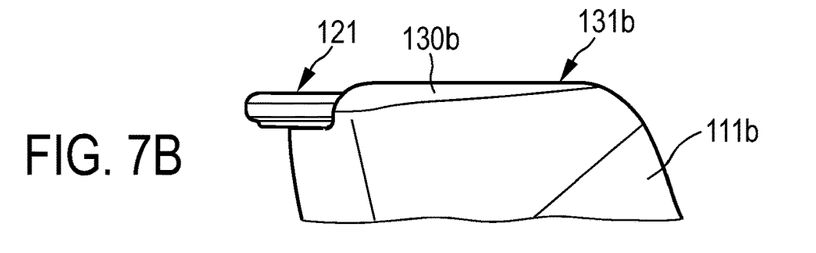
Figure 7C:
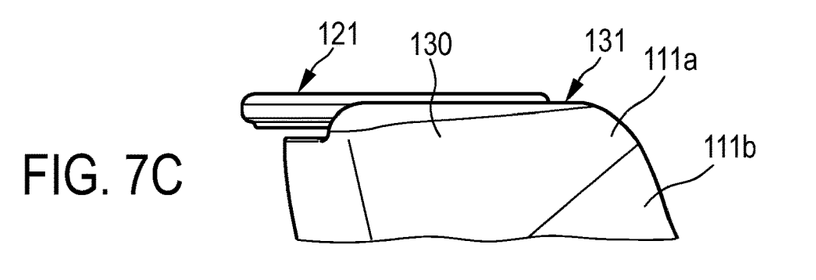

FIGS. 7a-c show a specific function incorporated in the treatment head of the first embodiment of the invention. As can be seen, the casing section 111 of the treatment head is divided up into two separate casing elements 111a, 111b. The protective rim 130 is unitary to the casing element 111a whilst the other casing element 111b is mounted to the handle section 110 of the housing. The casing section 111a and the protective rim 130 are releasably mounted such that a different protective rim 130b, which has a lower height, as shown in FIG. 7b, can be mounted instead of the protective rim 130 of FIG. 7a. By virtue of this, the skin contact surface 131 of the protective rim 130 may be adjusted to be flush with the axial abrasive treatment surface 121 as shown in FIG. 7a or the skin contact surface 131b of the protective rim 130b may be adjusted to protrude from the axial abrasive treatment surface 121 as shown in FIG. 7b. In other words, the protective rim 130 and the casing section 111a may be exchanged against the protective rim 130b such that the axial abrasive treatment surface 121 is recessed in the protective rim 130b as shown in FIG. 7b.

Further, as an alternative or additional function, the protective rim 130 and the casing section 111a may be maintained and the skin treatment element 120 may be slid somewhat outwards such that the axial abrasive treatment surface 121 protrudes from the protective rim 130, as shown in FIG. 7c. By this sliding movement of the protective rim 130 in relation to the skin treatment element, a regular position as shown in FIG. 7a, a position for increased control, as shown in FIG. 7b, and a position for increased ablation rate, as shown in FIG. 7c may be selected.

Figure 8:
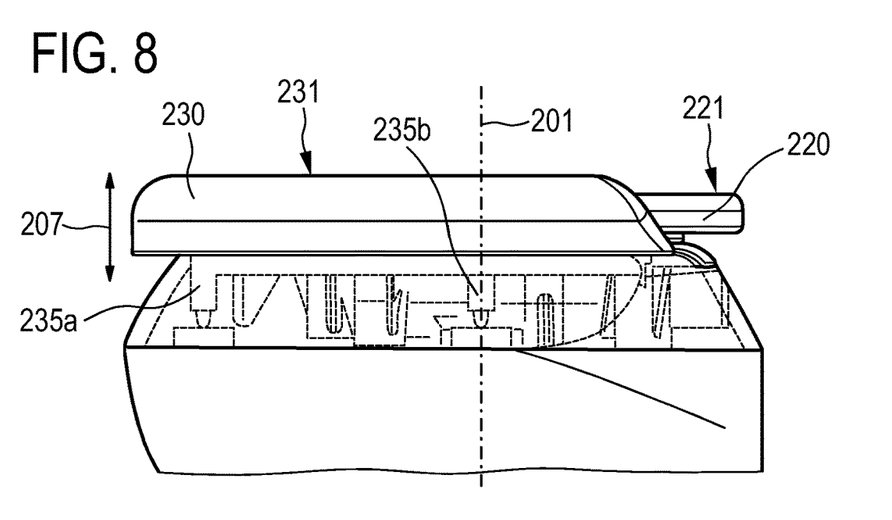
FIG. 8 shows a perspective partial side view of a second embodiment of the invention.

FIG. 8 shows a second embodiment of the invention. In this second embodiment the protective rim 230 generally is designed in the same way as the protective rim 130 of the first embodiment but is mounted to enable a sliding movement along the rotational axis 201 as depicted by arrow 207. The protective rim thus is embodied as a single, separate component and is not integral with the housing of the treatment head. The protective rim is guided along the rotational axis 201 by corresponding linear bearings 235a, b and furthermore is spring-biased into a protruding position depicted in FIG. 8. In this protruding position the axial abrasive treatment surface 221 is somewhat recessed in the protective rim and is positioned below a contact surface 231 of the protective rim to the skin. When using the second embodiment shown in FIG. 8, the user will bring the protective rim into contact with the skin region to be treated and will subsequently apply a manual force to apply pressure to the contact region between the contact surface 231 of the protective rim and the skin. Consequently, the protective rim will be slid somewhat inwards against the biasing force and thus the axial abrasive treatment surface will come into direct contact with the skin region to be treated. The user may control the pressure with which the treatment head is applied to the skin and thereby may adjust and balance the degree of control and the ablating rate by more or less forcing the protective rim to slide inwards against the biasing force.

Figure 9A:
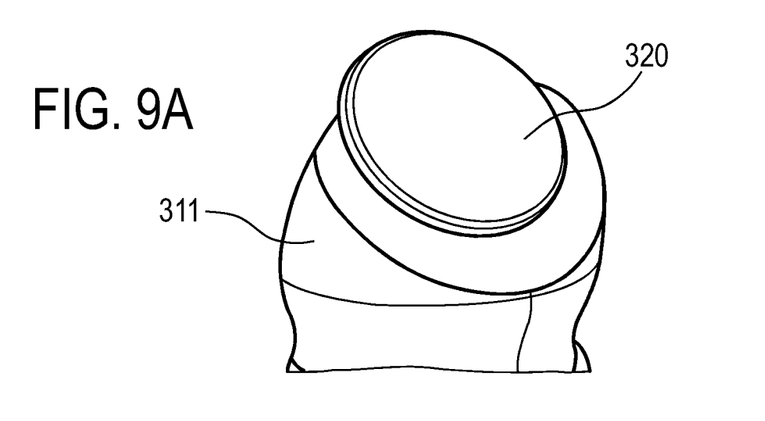
FIGS. 9a-c show a perspective partial top-side view of a third embodiment of the invention, FIGS. 10a,b show a perspective partial top-side view of a fourth embodiment of the invention depicting two different adjustments, FIG. 11 schematically shows a cross-sectional view of a fifth embodiment of the invention.
Figure 9B:
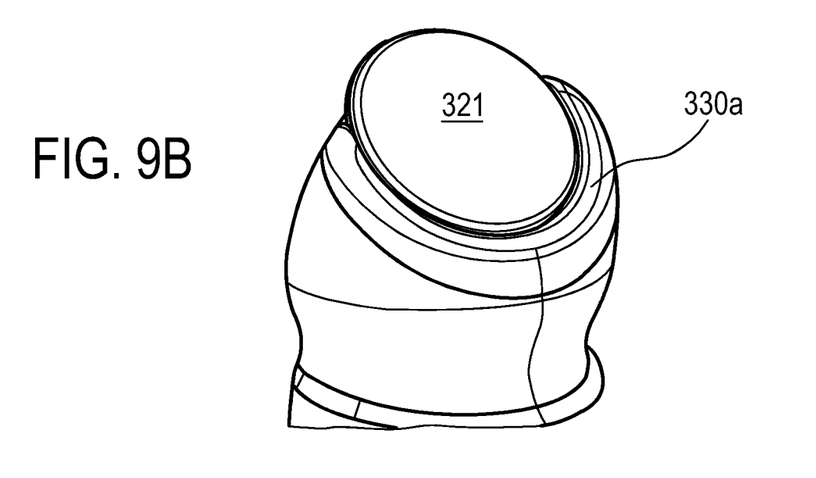
Figure 9C:
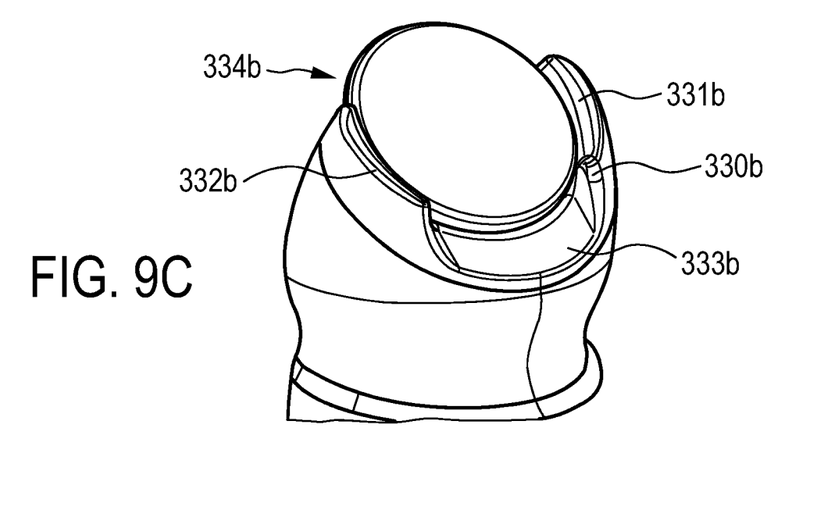

FIGS. 9a-c show a third embodiment of the skin treatment device according to the invention. As can be seen, the skin treatment device according to this third embodiment is configured to mount different protective rims 330a, 330b to the treatment head. FIG. 9a shows a configuration wherein no protective rim is mounted to the treatment head 311, which results in a protruding disk-shaped treatment element 320 allowing a very efficient ablating rate, but having a reduced control rate. FIG. 9b shows a protective rim 330a mounted to the treatment head and providing a partial circumferential encasing of the skin treatment element as described hereinbefore with reference to the first and the second embodiment. The protective rim 330a is designed to obtain a skin contact surface which is flush with the axial abrasive treatment surface in contact with the skin.

FIG. 9c shows a different protective rim 330b mounted to the treatment head. As can be seen, this protective rim 330b comprises a first and a second rim section 331b, 332b being arranged opposite to each other and thus providing two non-encased angular regions 333b, 334b of the skin treatment element. The first non-encased angular region 334b is identical to the non-encased angular region of 135° described with reference to the first and the second embodiment. The second non-encased angular region 333b is opposed to this first angular region and extends through approximately the same angle as the first angular region.

Figure 10A:
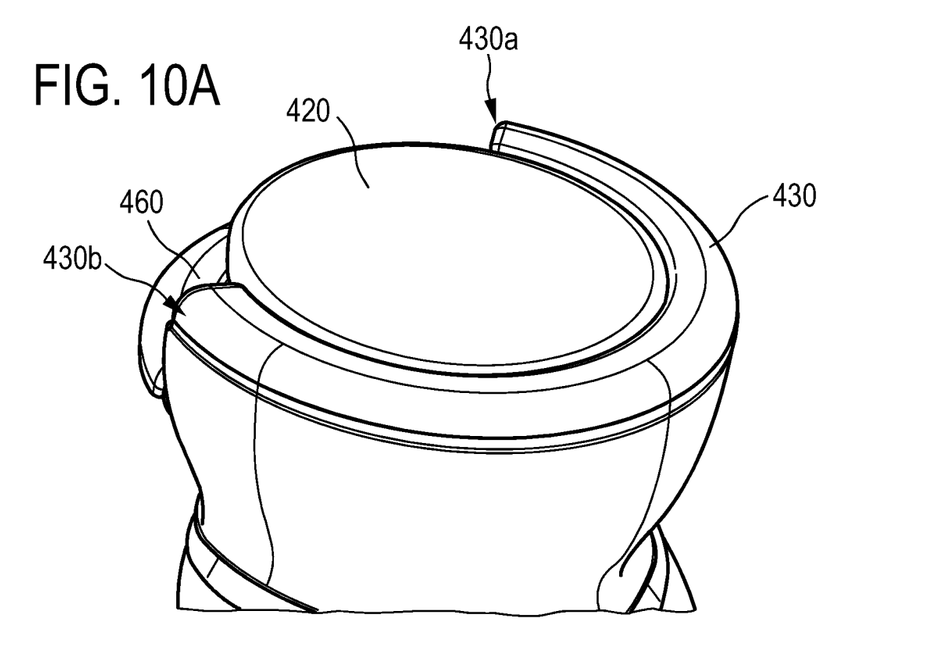
Figure 10B:
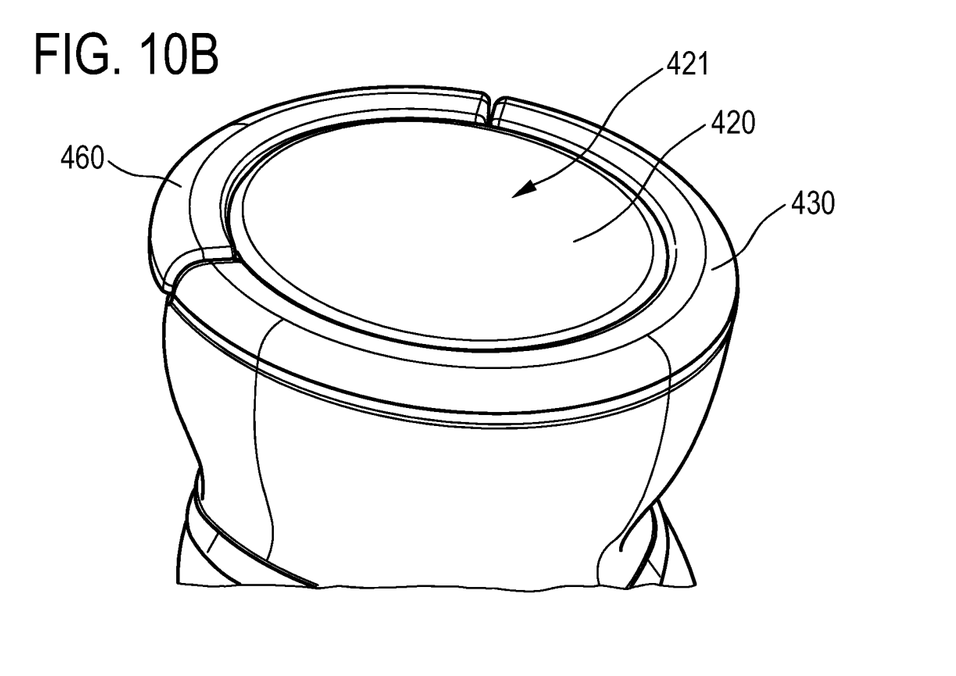

FIGS. 10a,b show a fourth embodiment of the invention. The skin treatment device according to this fourth embodiment comprises a protective rim 430 which is designed so as to be mainly identical to the protective rim 130 of the first embodiment shown in FIGS. 2-6, some design change being made at the angular end portions 430a,b of the protective rim which are designed to have a straight radial outline instead of the slightly rounded radial-tangential outline of the first embodiment. The fourth embodiment further comprises a protective rim element 460 which is shown in two positions and which can be switched between the first, recessed position shown in FIG. 10a and the second, flush position shown in FIG. 10b. The protective rim element 460 fills the angular gap left out by the protective rim 430 and thus, when switched into the second position shown in FIG. 10b, provides for a full encasement of the disk-shaped treatment element 420 throughout the periphery of 360°. Thus, in this second position, improved control for treatment of large surfaces is provided by the protective rim element 460.

To be switched into the first position shown in FIG. 10a, the protective rim element is slid along the direction of the rotational axis into a recessed position such that the skin treatment element 420 is encased only by the protective rim 430 and thus protrudes from the protective rim in an angular region of 135°. Thus, in this first position, the configuration is generally identical to the configuration provided by the protective rim 130 of the first embodiment, allowing a precision treatment by the protruding section of the skin treatment element 420. In particular, in this first position the circumferential abrasive treatment surface can be used for a precision treatment whilst in the second position shown in FIG. 10b this circumferential abrasive treatment surface is fully covered by the protective rim 430 and the protective rim element 460.

Figure 11:
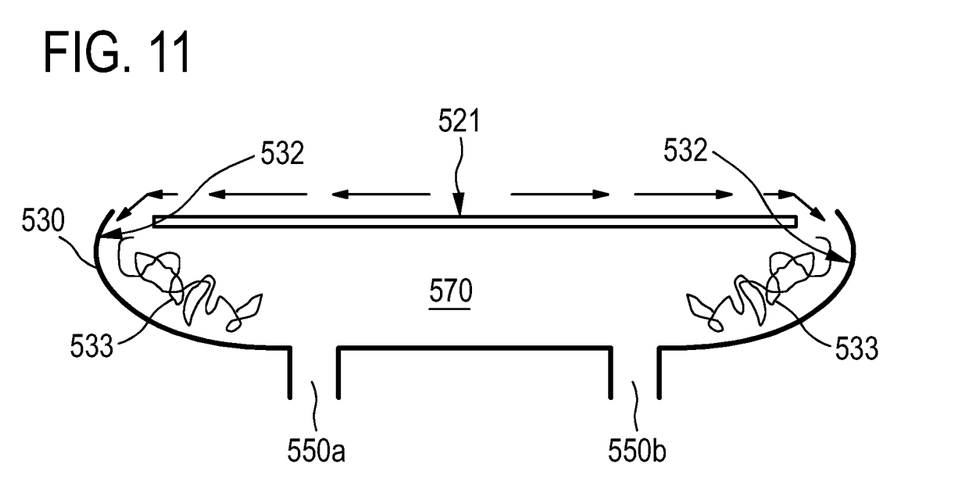

FIG. 11 explains in detail an additional function of the protective rim provided according to an embodiment of the invention. It is understood that this additional function may be provided by all four embodiments explained hereinbefore, namely by the protective rim or the protective rim element incorporated in these embodiments.

As can be seen, the protective rim is formed as a hollow-shaped shell element and thus provides an inner space 570. The protective rim 530 somewhat protrudes above the axial abrasive treatment surface 521 such that any dust or particles thrown off the axial abrasive treatment surface in a radial/tangential direction enter under the protective rim and are directed by the inner surface 532 of the protective rim into a circumferential dust collecting space 533 which is an outer circular region of the inner space 570. Particles and dust collected in the dust collecting space 533 may subsequently be discharged via channels 550a, 550b, wherein it is understood that these channels 550a, 550b correspond to the channels 150a, b shown in FIG. 6, into a dust collecting box or the like incorporated in the skin treatment device.

Figure 12A:
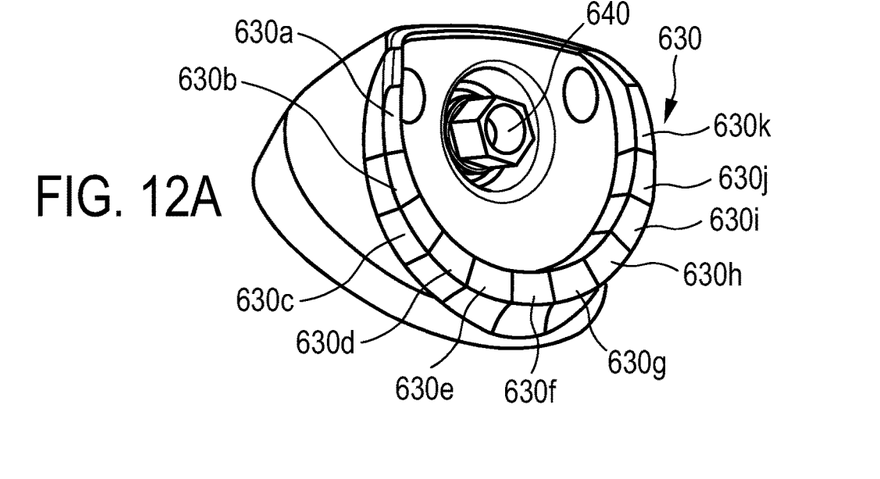
FIGS. 12a-c show a perspective view of a sixth embodiment of the invention depicting three different configurations.

FIG. 12a shows a detailed view of a treatment head of a sixth embodiment having a specific design of a protective rim extending over a partial angular range around a form-locking member 640 which is adapted for attachment of the skin treatment element. It is understood that this specific design may be incorporated in all five embodiments explained hereinbefore. The embodiment shown in FIG. 12a comprises a protective rim 630 which is composed of a plurality of rim segments 630a-k. In the embodiment shown in FIG. 12a, a total number of 11 rim segments form a continuous protective rim extending through an angular range of approximately 225° and leaving an open gap of approximately 135°. The two rim segments 630a, k adjacent to said gap and positioned at the respective ends of the protective rim are somewhat longer than the other rim segments 630b-j.

Each rim segment comprises an axially extending pin with a non-circular cross-section which is inserted into a corresponding opening 631a-k provided at the housing of the device. Each pin is releasably mounted and can be form-locked in such a corresponding opening. By virtue of this, a single segment or a plurality of segments may be moved relative to the other segments and removed from the housing.

Figure 12B:
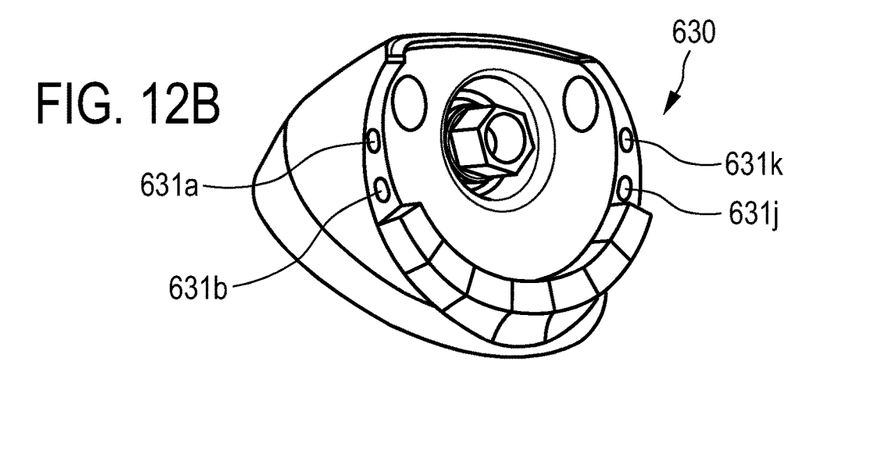

FIG. 12b shows a second configuration, wherein rim segments 630a,b and 630j, k were removed. As a result, the protective rim is composed of rim segments 630c-I only and thus the angular extension of the protective rim 630 is smaller in this second configuration than in the first configuration shown in FIG. 12a.

Figure 12C:
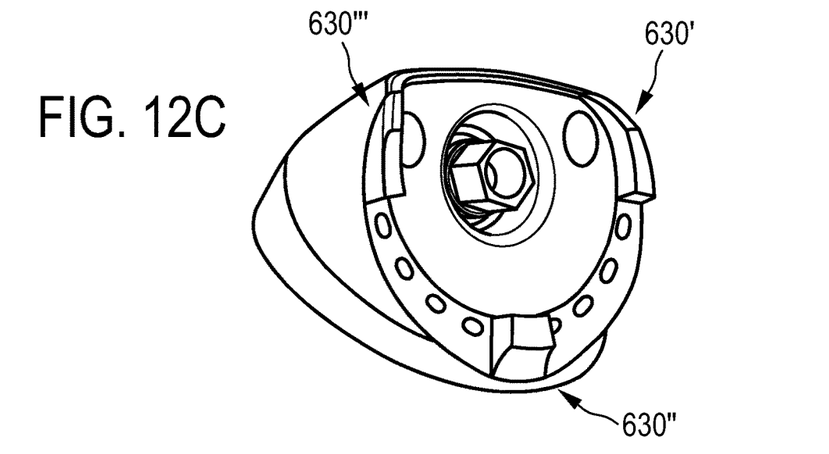

FIG. 12c shows a third configuration, wherein rim segments 630b-e and 630g-j were removed. As a result, the protective rim is composed of rim segments 630a, h and k only and thus forms three single protective rim regions 630', 630" and 630'" with a gap in between.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

Any reference signs in the claims should not be construed as limiting the scope.

The invention claimed is:

1. A skin treatment device, comprising:
a housing with a handle section and a treatment head section, wherein the handle section is in an angular orientation with respect to the treatment head section,
a skin treatment element rotatable around a rotational axis and configured to grind off a callus using an axial abrasive treatment surface and a circumferential abrasive treatment surface,
a protective rim arranged stationary at said treatment head section of the housing and having an axial skin contact surface configured and arranged to support the skin of a user along the axial direction during use, wherein said skin treatment element is rotatable in relation to said protective rim, and
a drive mechanism configured and arranged to drive the skin treatment element in a rotational movement about said rotational axis, wherein the axial abrasive treatment surface is accessible for skin treatment through an axial opening of the protective rim, wherein said axial opening extends over an angular range of 360° about said rotational axis,
wherein the skin treatment element is mounted to a shaft, the shaft is coupled to the drive mechanism in a releasable interlocking action,
wherein said skin treatment element is disk-shaped for rotational movement about the rotational axis,
wherein said circumferential abrasive treatment surface a portion that at least partially protrudes beyond the treatment head section of the housing in the radial direction,
wherein said protective rim partially and circumferentially encases said skin treatment element over an angular range of more than 120° and less than 330° about said rotational axis, such that the circumferential abrasive treatment surface is accessible for skin treatment in an area extending over an angular range of 30° to 240° about the rotational axis, and
wherein the axial skin contact surface of the protective rim and the axial abrasive treatment surface of the skin treatment element are configured to be adjustable relative to each other.

2. The skin treatment device according to claim 1, wherein an axial adjustment of a position of said skin treatment element and a position of said protective rim relative to each other in an axial direction parallel to said rotational axis is provided such that the position of the axial abrasive treatment surface in relation to the protective rim can be altered in said axial direction.

3. The skin treatment device according to claim 2, wherein said axial adjustment is provided by said skin treatment element or said protective rim being movable at least with a movement component parallel to said rotational axis.

4. The skin treatment device according to claim 2, wherein said axial adjustment is provided by
the protective rim being selected from a number of different, interchangeable protective rims to be mounted to said housing, wherein said interchangeable protective rims have mutually different heights parallel to said rotational axis; and/or
the skin treatment element being selected from a number of different, interchangeable skin treatment elements to be mounted to said housing, wherein said interchangeable skin treatment elements have mutually different heights parallel to said rotational axis.

5. The skin treatment device according to claim 1, wherein said protective rim comprises a circumferential inner edge, wherein said circumferential inner edge partially surrounds said skin treatment element and protrudes above or is flush with said axial abrasive treatment surface such that particles thrown radially outward along said axial abrasive treatment surface are collected by said inner edge and directed into a particle collecting space.

6. The skin treatment device according to claim 5, further comprising a conveying device for conveying particles collected in said collecting space to a collecting box.

7. The skin treatment device according to claim 6, wherein said conveying device is embodied as a fan driven by said drive mechanism.

8. The skin treatment device according to claim 7, wherein said conveying device is mounted rotatably about said rotational axis and driven synchronously with said skin treatment element.

9. The skin treatment device according to claim 1, wherein said skin treatment element protrudes radially outward of the treatment head section of the housing in said area in which the circumferential abrasive treatment surface is accessible for skin treatment.

10. The skin treatment device according to claim 1, wherein said skin treatment element is a disk-shaped abrasive tool having an abrasive treatment surface on an abutting axial surface forming the axial abrasive treatment surface and having an abrasive peripheral edge surface forming the circumferential abrasive treatment surface.

11. The skin treatment device according to claim 1, wherein said handle section extends along a handle axis and said rotational axis is oriented at an angle ($\square$) selected in a range of 20° to 90° relative to said handle axis; and
said skin treatment element is disk-shaped having an edge between the axial abrasive treatment surface and the circumferential abrasive treatment surface with an edge radius which is selected in a range of 0.3 mm to 10 mm; and
said skin treatment element is disk-shaped having a disk diameter which is selected in a range of 25 mm to 55 mm; and said drive mechanism is adapted to control a rotation speed of said skin treatment element to be in a range of 200 rpm to 1000 rpm; and said axial and circumferential abrasive treatment surfaces are each configured to form an abrasive surface having a grit size selected in a range of 80 to 200 according to the ANSI definition.

12. The skin treatment device according to claim 1, further comprising a protective rim element adapted to circumferentially encase said skin treatment element over an angular range of more than 30° and less than 240° about the rotational axis, respectively, to cooperate with said protective rim such as to fully encase said skin treatment element, wherein said protective rim element can be switched from a first position, wherein said skin treatment element is partially encased along its circumference by said protective rim, to a second position, wherein said skin treatment element s fully encased along its circumference by said protective rim and said protective rim element.

13. The skin treatment device according to claim 12, wherein said switching from said first to said second position and vice versa is provided by said protective rim element being releasably mounted to said housing or being movable in relation to said housing.

14. The skin treatment device according to claim 1, wherein said protective rim is movable in a direction parallel to said rotational axis and biased towards an outward position wherein said protective rim axially projects above said skin treatment element along said rotational axis.

15. The skin treatment device according to claim 1, wherein said protective rim comprises a plurality of rim segments which are movable relative to each other.

16. The skin treatment device according to claim 1, wherein the skin treatment element protrudes radially outward of the treatment head section of the housing in said area extending over said angular range of 30° to 240°0 about the rotational axis.

17. The skin treatment device according to claim 1, wherein the skin treatment element has an edge between the axial abrasive treatment surface and the circumferential abrasive treatment surface with an edge radius which is selected in a range of 0.3 mm to 10 mm.

18. The skin treatment device according to claim 17, wherein the edge radius is selected in a range of 1.0 mm to 5.0 mm.

19. The skin treatment device according to claim 1, wherein the disk-shaped element has a disk diameter which is selected in a range of 30 mm to 36 mm.

20. The skin treatment device according to claim 1, wherein the rotational axis is in angular orientation with respect to a handle axis along which the handle section extends.

* * * * *